United States Patent
Burattini et al.

(10) Patent No.: US 8,729,315 B2
(45) Date of Patent: May 20, 2014

(54) PROCESS FOR THE PREPARATION OF PHENOL FROM CUMENE

(75) Inventors: Mauro Burattini, Cornaredo (IT); Roberto Bagatin, Legnano (IT)

(73) Assignee: Versalis S.p.A., San Donato Milanese (IT)

( * ) Notice: Subject to any disclaimer, the term of this patent is extended or adjusted under 35 U.S.C. 154(b) by 164 days.

(21) Appl. No.: 13/508,619

(22) PCT Filed: Oct. 29, 2010

(86) PCT No.: PCT/IB2010/002778
§ 371 (c)(1), (2), (4) Date: Jul. 12, 2012

(87) PCT Pub. No.: WO2011/055206
PCT Pub. Date: May 12, 2011

(65) Prior Publication Data
US 2012/0283486 A1    Nov. 8, 2012

(30) Foreign Application Priority Data

Nov. 9, 2009    (IT) .............................. MI2009A1956

(51) Int. Cl.
*C07C 37/08*    (2006.01)

(52) U.S. Cl.
USPC ........................................ 568/798; 568/802

(58) Field of Classification Search
USPC ................................. 568/798, 802
See application file for complete search history.

(56) References Cited

U.S. PATENT DOCUMENTS

| | | |
|---|---|---|
| 3,161,476 A | 12/1964 | Lemetre et al. |
| 2005/0177004 A1 | 8/2005 | Codignola |
| 2007/0260093 A1 | 11/2007 | Kuma et al. |
| 2009/0005606 A1 | 1/2009 | Hassan et al. |
| 2009/0171126 A1* | 7/2009 | Zakoshansky et al. ....... 568/569 |
| 2011/0096618 A1* | 4/2011 | Le ................................ 366/101 |

FOREIGN PATENT DOCUMENTS

WO    03 076376    9/2003

OTHER PUBLICATIONS

International Search Report Issued Feb. 10, 2011 in PCT/IB10/02778 Filed Oct. 29, 2010.

* cited by examiner

*Primary Examiner* — Sudhakar Katakam
*Assistant Examiner* — Pancham Bakshi
(74) *Attorney, Agent, or Firm* — Oblon, Spivak, McClelland, Maier & Neustadt, L.L.P.

(57) ABSTRACT

Process for the production in continuous or semi-continuous of phenol/acetone from cumene, via cumene hydroperoxide (CHP), which comprises: a. producing CHP in an air-lift reactor in which at least the upper and/or lower part of the downcomer has a flaring; b. cleaving the cumene hydroperoxide by means of acid treatment in a loop reactor comprising two heat exchangers connected in series and wherein the feedings of CHP and fresh acetone are in pairs and each pair is positioned up-stream of each exchanger.

11 Claims, 4 Drawing Sheets

PROCESS FOR THE PREPARATION OF PHENOL FROM CUMENE

CROSS-REFERENCE TO RELATED APPLICATIONS

This application is a National Stage of PCT/IB2010/002778 filed on Oct. 29, 2010. This application is based upon and claims the benefit of priority to Italian Application MI2009A 001956 filed on Nov. 9, 2009.

BACKGROUND OF THE INVENTION

The present invention relates to a process for the preparation of phenol from cumene.

As is known, phenol can be produced from cumene. The production process takes place in two phases. In the first phase, the cumene is oxidized to cumene hydroperoxide (CHP), with conversions which range from 20-35% by weight, in the second phase the CHP is acid cleaved into phenol and acetone with an acid, generally sulfuric acid. Between the first and second phase, there is generally a concentration step in which the CHP is concentrated to 70-90% by weight.

At the end of the acid cleaved reaction, which is extremely exothermic, the reaction mass is neutralized and the phenol is then recovered by distillation.

Since both the oxidation reaction and the subsequent acid cleaved reaction are accompanied by undesired secondary reactions, it is necessary to arrange methods/equipment, for carrying out the two operative stages described above, which can limit this drawback. In particular, by-products are produced through the secondary reactions as, for example, dicumyl peroxide (DCP) and dimethyl benzyl alcohol (DMBA) which, after downstream treatments, are selectively transformed into phenol and alpha-methylstyrene. The latter, after hydrogenation, forms cumene and can then be recycled.

Industrially, the oxidation reaction of cumene is effected by means of specific reactors, known as "air-lift" reactors, substantially consisting of a cylindrical structure inside which a second cylinder, open at the ends, is coaxially positioned, which allows the internal recirculation of the reaction mass. Said second cylinder is known by experts in the field, with the term "downcomer". An example of an air-lift reactor is provided in FIG. 1A, which illustrates the essential elements of the reactor comprising the outer mantle, the downcomer and the feeding/discharge points of the reagents and reaction products in addition to the gas and vapours vents.

The reagents, cumene and a gas containing oxygen, preferably air, are fed to the base of the reactor in continuous and are recycled, again continuously, in the interior through the downcomer. A gas phase, consisting substantially of residual air and vapours, is discharged from the head of the reactor together with the reaction product, a mixture consisting essentially of CHP and non-reacted cumene, in addition to possible by-products.

After concentration in CHP, the reaction product can be temporarily stored and is then subjected to a cleavage reaction. On an industrial scale, this second reaction takes place in a closed cycle reactor known to experts in the field as "loop" reactor. In particular, this reactor, represented in FIG. 2, consists of tube A in which there is an inlet of the acid component (1) and an inlet, upstream of this, of CHP (2) and acetone (3). The acetone, which is one of the two products deriving from the cumene hydroperoxide cleavage, is introduced with the function of reaction moderator, in order to increase the overall yield of the process. The reaction mixture then rapidly passes in the tubes of a tube-bundle reactor (B), while the heat of reaction is removed with cooling water, fed and dischrged through (4) and (5), flowing on the shell side. The reaction mixture is re-fed to the tube (A) and the cycle continues. The phenol produced (together with the acetone) is discharged in continuous from (6).

The Applicant has now found a process for the production of phenol from cumene which is alternative to the process known in the state of the art. This new process, as far as the oxidation phase is concerned, improves selectivity to CHP and is simpler to manage as, for example, it allows a better control of the temperature in favour of the safety. As far as the cleavage reaction is concerned, the process has lower management costs, due to a smaller load to be processed by the recirculation pump, and higher selectivities to phenol and alpha-methylstyrene.

BRIEF SUMMARY OF THE INVENTION

An object of the present invention therefore relates to a process for the production in continuous or semi-continuous of phenol from cumene, via cumene hydroperoxide (CHP), which comprises:

a. producing CHP by the oxidation of cumene with a gas containing oxygen in an air-lift reactor comprising:
   a1. a cylindrical structure equipped with lower and upper closing elements, said elements being respectively provided with means for feeding the reagents and means for discharging the reaction products (substantially CHP), vapours and non-reacted gas;
   a2. a second substantially cylindrical structure (downcomer), open at the ends (bases), inside and coaxial with the first structure; and
   a.3 a toroidal gas distributor situated at the base of the reactor around the second substantially cylindrical structure;

characterized in that the downcomer is provided with at least one upper and/or lower flaring so that the A1/A2 ratio, between the larger transversal section A1 and the smaller transversal section A2 of said flaring, ranges from 1.1 to 2;

b. concentrating the solution containing CHP, discharged from the air-lift reactor, to at least 70% by weight, preferably from 80 to 90%;

c. producing phenol by acid cleaved reaction of CHP, in the presence of acetone, in a loop reactor where the reaction heat is recovered in two heat exchangers arranged in series in the cycle;

characterized in that the feedings of CHP and acetone are in pairs and each pair is positioned upstream of each exchanger.

DETAILED DESCRIPTION OF THE INVENTION

Figure 1A:
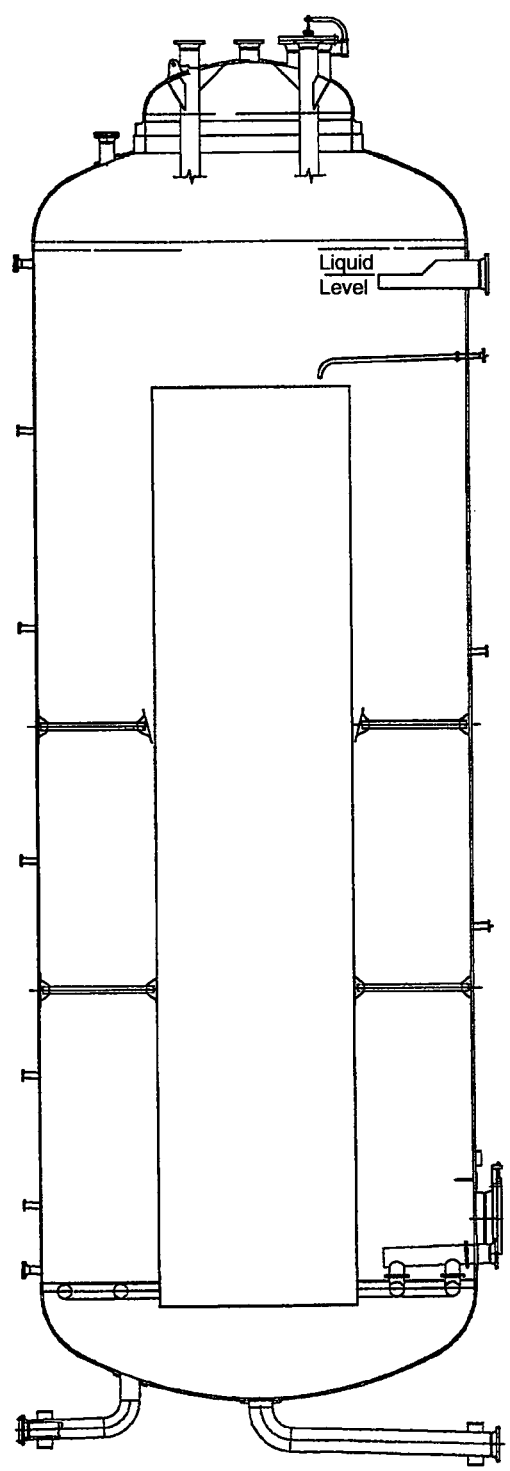
FIG. 1A depicts one example of an air-lift reactor.
Figure 1B:
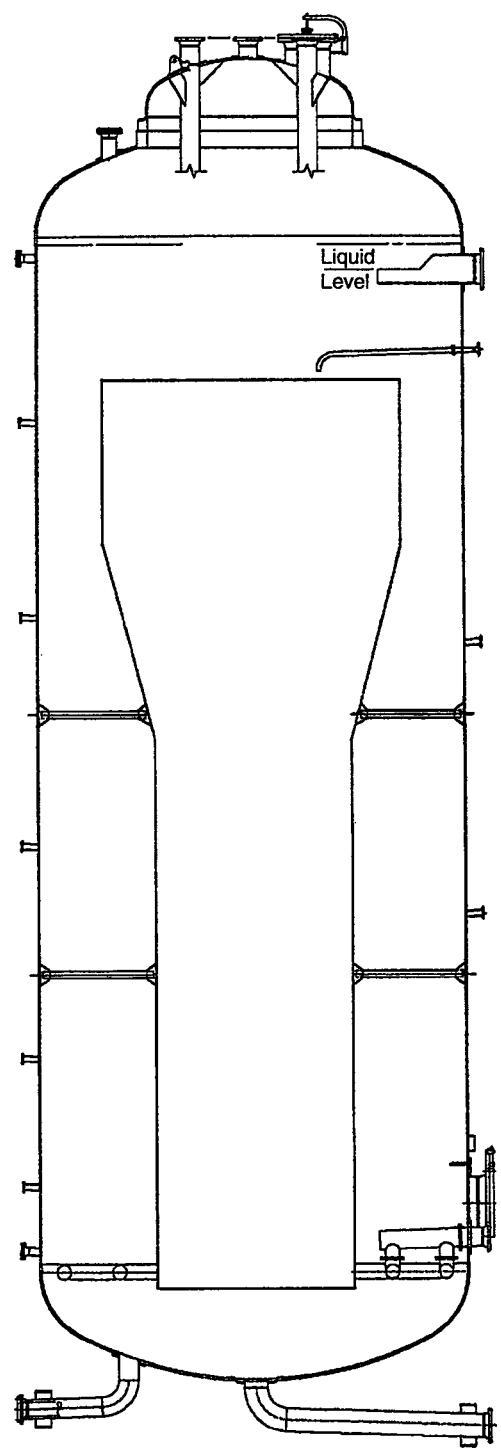
FIG. 1B is a schematic of one embodiment of an air-lift reactor of the present invention.
Figure 2:
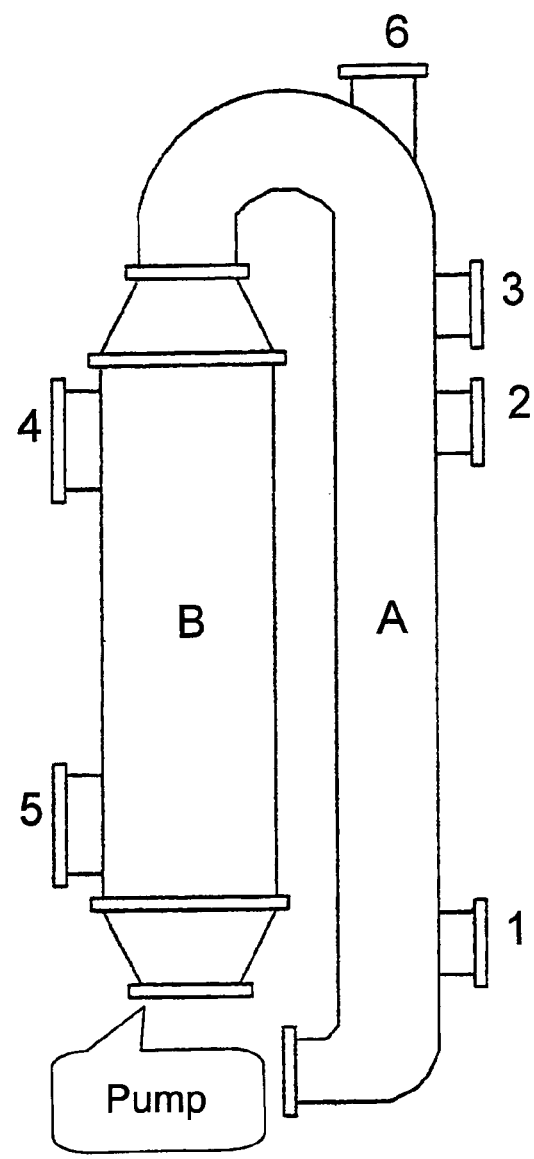
FIG. 2 depicts one example of a loop reactor.

According to the present invention, the air-lift reactor of which a schematic representation is illustrated in FIG. 1B, where the innovative element (flaring) with respect to the equivalent device of the known art, is evident, is fed with air possibly enriched in oxygen, for example up to 50% by volume. Alternatively, for safety reasons, it is possible to operate with air at a reduced concentration of oxygen, for example 10-20% by volume. The oxidation reaction of the cumene takes place at a temperature ranging from 50 to 150° C. and at a pressure ranging from 0.1 to 0.8 MPa.

The air is fed by means of the toroidal distributor equipped with a plurality of holes. The distributor is positioned at the base of the reactor and allows the air fed to flow upwards, touching the walls of the mantle, in the form of bubbles. When it has reached the head of the reactor, a part of the air is discharged into the outside, whereas another part is recycled, as it is entrained by the liquid, and descends into the downcomer. This recirculation movement is considerably favoured by the flaring of the downcomer which allows a recycling ratio of the air inside the downcomer, defined as the ratio between the quantity (in volume) recirculating and the quantity (in volume) which leaves the reactor, higher than 0.3, preferably from 0.4 to 0.7, thus increasing the oxidation selectivity.

The downcomer is substantially a tube or cylindrical element positioned coaxially inside the reactor and, as it is open at the ends (bases), it allows the reagent system, and in particular the air, to recirculate with a cyclic descending movement, in the central part of the reactor, and upward movement, along the riser of the reactor.

The flaring of the downcomer can be positioned in the upper part of the cylindrical element and/or in the lower part. In both cases, the flarings can also start from one base and end in correspondence with the other base of the cylindrical element. It is preferable, however, for the flaring to initiate starting from about half of the length of the tube, for example it is preferable for the flaring to involve 10-40% of the length of the tube, starting from one or both bases or ends. In both cases, the term flaring refers to the broadening of the section of the tube or cylindrical element or downcomer towards the upper and/or lower base.

According to a preferred embodiment of the present invention, it is possible to join a cylindrical ring to the top of the flaring of the downcomer, upper and/or lower, whose height, although depending on the dimensions of the reactor, can range, for example, from 5 to 100 cm.

According to a further embodiment of the present invention, the outer mantle of the oxidation reactor of the cumene can also comprise a similar upward and/or downward flaring which resumes and substantially corresponds to the flaring of the downcomer.

Finally, the oxidation reaction of cumene is preferably effected in the presence of basic compounds. Examples of basic compounds are amines, hydroxides and carbonates of alkaline metals such as lithium, sodium, potassium, or alkaline-earth metals such as calcium and magnesium, used alone or mixed with each other. The hydroxides and carbonates can generally be fed as aqueous solutions/dispersions with such flow-rates that the amount of base metal ranges from 0.1 to 10, preferably from 0.5 to 8, equivalent grams per ton of cumene fed. The same concentration is valid for the amines.

The CHP produced is discharged continuously from the air-lift reactor and, after concentration, can be stored (semi-continuous process) before being sent to the scission reaction.

The concentration of CHP, to values higher than 70% by weight, takes place by evaporation/distillation in specific equipment. The concentrated product is fed to the production section of phenol (and acetone as by-product).

The acid cleaved reaction takes place in the presence of further acetone and an acid, preferably an inorganic acid such as sulfuric, phosphoric or nitric acid. The acetone, which is also a by-product of the acid cleaved reaction, is used with diluent functions whereas the acid is the catalyst which favours the acid cleavage, extremely exothermic, of the CHP to phenol and acetone. The acid is fed into the cycle in a single step.

The concentration of acid in the reaction medium ranges from 80 to 250 ppm, preferably from 110 to 180 ppm, and is more preferably 150 ppm.

As the acid cleaved reaction of CHP is extremely exothermic, the reaction heat must be rapidly disposed of. For this reason, the reaction system comprises two tube-bundle exchangers cooled externally. Each tube bundle is situated in a container, for example cylindrical, fed with a cooling fluid, for example water, fed and discharged with a continuous flow. The cooling liquid substantially occupies the free volume of the exchangers not occupied by the tube bundle.

The two exchangers, arranged in the cycle, are connected to each other so that the outlet of one becomes the feeding of the other, and vice versa.

The feedings of CHP and acetone are positioned in pairs upstream of each heat exchanger. In particular, with the first feeding pair, from 0 to 100% of CHP and/or acetone, preferably from 30 to 70%, more preferably 50% are fed, and from 100 to 0% of CHP and/or acetone, preferably from 70 to 30%, more preferably 50%, are fed correspondingly, by means of a second feeding pair.

Figure 3:
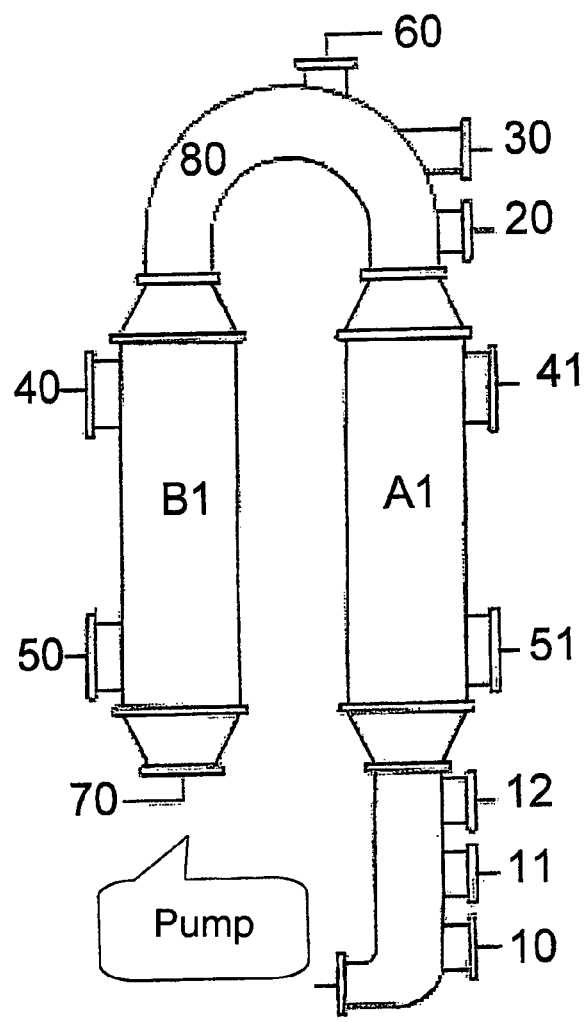
FIG. 3 depicts an illustrative scheme of one embodiment of a reaction system for a scission system of the present invention.

FIG. 3 shows an illustrative scheme of the reaction system for the scission reaction of CHP according to the present invention. The system comprises two tube-bundle heat exchangers A1 and B1, connected to each other by means of the U-tube (80) and the system (70), comprising the pump, which allow the continuous recirculation of the reaction flow which leaves the tubes of a tube bundle (for example that in A1) so that it enters the subsequent tube bundle (B1). The two tube bundles are contained in cylindrical containers inside which cooling water circulates, fed and discharged by means of (40), (50) and (41), (51) respectively.

The feedings of the whole of the acid (10) and part of the CHP (11) and acetone (12) respectively, are present in the tube of the system (70). The second and remaining part of CHP and acetone is fed to the loop reactor by means of (20) and (30) respectively.

The reagent mixture circulates continuously in the loop reactor using the recirculation pump. The reaction product, phenol in an acetone solution, is discharged continuously from the outlet (60).

According to an alternative embodiment of the loop reactor in accordance with the present invention, the acid can be pre-diluted in the acetone, in particular in one of the two partialized feedings.

The invention claimed is:

1. A process for continuous or semi-continuous production of phenol from cumene, via cumene hydroperoxide (CHP), which comprises:
   a. producing CHP by the oxidation of cumene with a gas containing oxygen in an air lift reactor comprising:
      a1. a cylindrical structure equipped with lower and upper closing elements, said elements being respectively provided with means for feeding the reagents and means for discharging the reaction products (substantially CHP), vapours and non-reacted gas;
      a2. a second substantially cylindrical structure (downcomer), open at the ends (bases), inside and coaxial with the first structure; and
      a.3 a toroidal gas distributor situated at the base of the reactor around the second substantially cylindrical structure;

the production of CHP being characterized in that the downcomer is provided with an upper and/or lower flaring so that the A1/A2 ratio, between the larger transversal section A1 and the smaller transversal section A2 of said flaring, ranges from 1.1 to 2;
b. concentrating the solution containing CHP, discharged from the air lift reactor, to at least 70% by weight;
c. producing phenol by acid cleaved reaction of CHP, in the presence of acetone, in a loop reactor where the reaction heat is recovered in two heat exchangers arranged in series in the cycle;

the production of phenol being characterized in that the feedings of CHP and acetone are in pairs and each pair is positioned upstream of each exchanger.

2. The process according to claim 1, wherein the air lift reactor is fed with air, optionally enriched up to 50% by volume of oxygen.

3. The process according to claim 1, wherein the air lift reactor is fed with air at a reduced oxygen concentration ranging between 10 and 20% by volume.

4. The process according to any one of the previous claims, wherein the oxidation reaction of cumene takes place at a temperature ranging from 50 to 150° C. and at a pressure ranging from 0.1 to 0.8 MPa.

5. The process according to claim 1, wherein a cylindrical ring, whose height ranges from 5 to 100 cm, is joined to the top of the upper and/or lower flaring of the downcomer.

6. The process according to claim 1, wherein the outer shell of the oxidation reactor of cumene comprises a similar upward and/or downward flaring which substantially corresponds to the flaring of the downcomer.

7. The process according to claim 1, wherein the recycling ratio of the air inside the downcomer, defined as a ratio between the recirculating quantity and the quantity leaving the reactor, is higher than 0.3.

8. The process according to claim 1, wherein the oxidation reaction of cumene is effected in the presence of basic compound selected from amines and hydroxides and carbonates of alkaline metals or alkaline-earth metals.

9. The process according to claim 8, wherein the hydroxides and carbonates of alkaline or alkaline-earth metals are fed as aqueous solutions/dispersions with flow-rates which are such that the quantity of base metal ranges from 0.1 to 10 gram equivalents per ton of cumene fed.

10. The process according to claim 1, wherein the CHP is concentrated to values ranging from 80 to 90% by weight by means of evaporation/distillation.

11. The process according to claim 1, wherein the acid cleaved reaction takes place in the presence of acetone and an acid selected from sulfuric, phosphoric or nitric acid.

* * * * *